United States Patent [19]
Adams et al.

[11] Patent Number: 5,466,851
[45] Date of Patent: Nov. 14, 1995

[54] DETERGENT PRODUCTION

[75] Inventors: Amanda J. Adams; Philip S. Jackson; Howard N. Moulden; David W. Roberts, all of Wirral; Keith Watkin, Surrey, all of United Kingdom

[73] Assignee: Lever Brothers Company, Division of Conopco, Inc., New York, N.Y.

[21] Appl. No.: 167,260

[22] Filed: Dec. 14, 1993

[30] Foreign Application Priority Data

Dec. 14, 1992 [GB] United Kingdom .................. 9226003

[51] Int. Cl.$^6$ ................................................. C07C 305/06
[52] U.S. Cl. ............................... 558/21; 558/41; 558/31; 558/34
[58] Field of Search ........................ 558/21, 41, 31, 558/34

[56] References Cited

U.S. PATENT DOCUMENTS

| | | |
|---|---|---|
| 2,098,114 | 11/1937 | Suter . |
| 2,923,728 | 2/1960 | Falk et al. . |
| 3,755,407 | 8/1973 | Wilkes . |
| 4,464,292 | 8/1984 | Lengyel . |

FOREIGN PATENT DOCUMENTS

| | | |
|---|---|---|
| 1123709 | 8/1968 | United Kingdom . |
| 1453774 | 10/1976 | United Kingdom . |
| WO91/13057 | 9/1991 | WIPO . |

*Primary Examiner*—Nicky Chan
*Attorney, Agent, or Firm*—James J. Farrell

[57] ABSTRACT

A method of preparing PAS acid is disclosed which involves sulphating an alcohol feedstock and incorporating in the reaction product, a stabilizing agent which comprises an (hydroxy) alkylene oxide residue.

8 Claims, No Drawings

DETERGENT PRODUCTION

This invention relates to the production of compounds of the general formula:

$$ROSO_3H$$

where R denotes a primary alkyl group. The compounds are primary alkyl half esters of sulphuric acid. They are the acid form of primary alkyl sulphate, variously known as primary alcohol sulphate, which is an anionic detergent.

Primary alkyl sulphate (PAS) of formula:

$$ROSO_3M$$

where
R is a straight or branched alkyl chain of 8 to 20 carbon atoms, and
M is a solubilising cation such as sodium or ammonium
has been known for very many years as an anionic detergent.

Primary alkyl sulphate is customarily produced by sulphation of the corresponding primary alcohol so as to produce the acid form of the detergent (PAS acid).

This acid form is then neutralised to the detergent itself so that the production route is $$ROH \rightarrow ROSO_3H \rightarrow ROSO_3M$$

Sulphation of the primary alcohol can be carried out using sulphur trioxide in conventional apparatus for sulphation/sulphonation reactions.

A known problem, however, is that the resulting PAS acid is unstable and spontaneously reverts to the primary alcohol. If the PAS acid is stored at ambient temperature a substantial proportion will decompose to the starting alcohol within 24 hours. Moderate cooling below ambient temperature reduces the amount of decomposition but it still remains a problem. Consequently it is necessary to neutralise the PAS acid promptly after it has been made by the sulphation reaction. This reduces flexibility in operating the overall production process. It is moreover inconvenient because the physical properties of PAS acid would make it easier to handle and transport than the paste which results from neutralisation.

When the spontaneous decomposition of PAS acid occurs it leads to the formation of the original primary alcohol which was the starting material for the sulphation and also to sulphuric acid. If the mixture is neutralised and analysed it is found to contain the desired primary alkyl sulphate, an inorganic salt such as sodium sulphate resulting from neutralisation of the sulphuric acid which is the product of decomposition and also the primary alcohol which results from decomposition. The customary analysis normally reports a percentage of so-called non-detergent organic matter (NDOM) often referred to as "free oil" (FO) which includes the primary alcohol decomposition product and also any primary alcohol starting material which did not react during sulphation.

As will be explained below the invention may make use of compounds containing alkylene oxide residues—the presence of these can lead to the introduction of trace quantities of dioxan compounds whose presence in the product is undesirable.

The present invention aims firstly to inhibit the spontaneous decomposition of PAS acid. Preferred forms of the invention seek to do so while also keeping dioxan impurities at low levels.

Broadly we have now found that the spontaneous decomposition of PAS acid can be effectively inhibited by the presence of alkylene oxide residues, which may also be termed alkyleneoxy groups, and hydroxyalkyleneoxy groups.

Broadly, according to a first aspect of this invention there is provided a method of preparing and stabilising primary alkyl sulphuric acid having the formula:

$$ROSO_3H$$

where R is a saturated straight or branched primary alkyl group of 8 to 22 carbon atoms which method comprises sulphating a feedstock comprising the corresponding primary alcohol of formula:

$$ROH$$

to produce a sulphated reaction product, and incorporating in the sulphated reaction product, as a stabilising agent, one or more compounds which include alkylene oxide residues or hydroxyalkyleneoxy groups, the proportion of the alcohol ROH in the feedstock exceeding the proportion, if any, of compounds which include alkylene oxide residues or hydroxyalkyleneoxy groups.

The invention leads to a mixture containing the said primary alkyl sulphuric acid and the stabilising agent. Such a mixture represents a further aspect of this invention.

The amount of the stabilising agent will usually be less than the amount of the primary alkyl sulphuric acid. In particular the weight ratio of primary alkyl sulphuric acid to stabilising agent may lie in a range from 20:1 to 2:1.

The group R may well be a saturated alkyl group having 8 to 15 carbon atoms,

Usually the primary alkyl group R will be a mixture of saturated, straight or branched alkyl chains averaging 11 to 18 carbon atoms, the range from 12 to 15 carbon atoms being particularly significant.

The stabilising agent may be a wide variety of compounds which can be represented by a general formula:

$$Y(A)_nX$$

where A represents an alkylene oxide residue or a hydroxyalkyleneoxy group, n is positive and Y and X can be a substantial variety of terminal groups. Without wishing to be bound by any theory as to the mode of action of the stabilising agent, it is believed that stabilisation is brought about through oxygen atoms which are ether linkages and which are provided by the alkylene oxide residues or hydroxyalkyleneoxy groups. These ether oxygen atoms are believed to transiently bind hydrogen ions and prevent those ions from participating in a decomposition pathway of the primary alkyl sulphate. This does not, of course, exclude the possibility of some other stabilising action being operative simultaneously or alternatively, in particular in the event that Y or X is hydrogen so that the stabilising agent has a hydroxyl group which may well participate in an alternative mechanism of stabilisation.

It is preferred that the stabilising agent incorporates residues of an alkylene oxide containing from 2 to 4 carbon atoms, notably ethylene oxide.

An alkylene oxide residue can also be termed an alkyleneoxy group, of formula:

$$-(OW)-$$

where W represents a divalent alkylene group. A hydroxyalkyleneoxy group is of formula:

where

is a hydroxy substituted alkylene group, notably hydroxypropyl or hydroxyisopropyl.

It is also preferred that the stabilising agent should have surfactant properties. Then it can serve as an additional detergent in a detergent product which incorporates the primary alkyl sulphate obtained by eventual neutralisation its acid form.

Preferred stabilising agents therefore are compounds and mixtures of compounds which comply with a general formula:

$$R^1(A)_n X$$

where $R^1$ is a straight or branched primary alkyl group of 8 to 22 carbon atoms, A is as defined before and X is hydrogen, $-OSO_3H$ or an alkyl group of 1 to 8, preferably 1 to 4, carbon atoms. Where X is an alkyl group, for example methyl dioxan formulation may be beneficially suppressed. The average value of n may lie in the range from 0.5 to 4 or possibly higher, e.g. 0.5 to 10 or more. More preferably the value of n is at least 1. It may be preferred that the value of n is not over 3. A range from 1.5 to 2.5 is particularly envisaged. $R^1$ may well be saturated alkyl with an average chain length of not more than 18 carbon atoms. It may contain an average of at least 11 carbon atoms, and preferably 11 to 15 carbon atoms.

As already mentioned, the amount of stabilising agent will usually be less than the amount of PAS acid. The weight ratio of acid to stabilising agent will preferably lie in a range from 20:1 to 1.5:1. The amount of stabilising agent may be sufficient that the range does not extend beyond 10:1 or even 9:1. At the other end of the range the amount of stabilising agent may be such that the range does not go beyond 3:1 or even 4:1.

Preferably the ratio by number of PAS acid molecules to alkylene oxide residues or hydroxyalkyleneoxy groups of the stabilising agent is greater than 1:1, i.e. PAS acid molecules outnumber alkylene oxide residues and hydroxyalkyleneoxy groups.

Sulphation is preferably carried out using sulphur trioxide.

The invention is not limited to any specific apparatus for carrying out the chemical reaction by which PAS acid is formed. Conventional practice is to effect sulphonation using sulphur trioxide in a reactor which provides a high surface area for contact between the reactants. A falling film reactor is normally used.

The stabilising agent may be added to the PAS acid after the sulphation has been carried out. Alternatively or in addition, the stabilising agent or a precursor of it may be added to the primary alcohol before sulphation takes place, or even during the course of sulphation if the apparatus will permit this.

It is preferred for the sake of reducing the dioxan impurities, that stabilising agent is added after sulphation has taken place even if some has been incorporated prior to or during sulphation. The addition preferably occurs promptly after the PAS acid leaves the reactor in which the sulphation occurs. Desirably it is added after not more than 15 minutes, better after not more than 5 minutes.

Preferred stabilising agents for addition after sulphation has occurred are compounds and mixtures of compounds of the formula:

where A denotes an alkylene oxide residue having from 2 to 4 carbon atoms, and X is hydrogen or an alkyl group of 1 to 8, preferably 1 to 4 carbon atoms, while $R^1$ and n are as defined previously.

If the stabilising agent of formula $R^1(A)_n OX$ is a material in which X denotes hydrogen, some of it may be sulphated very quickly by residual sulphur trioxide contained in the PAS acid. The resulting product of formula:

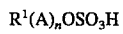

is the acid form of alkyl ether sulphate which can also serve as anionic detergent following neutralisation, especially if A denotes an ethylene oxide residue.

Stabilising agents of formula $R^1(A)_n OX$ in which X denotes hydrogen are nonionic surfactants. Stabilising agent of this type which does not react prior to neutralisation will therefore provide a content of nonionic surfactant in the neutralised mixture and in products made from it.

If the stabilising agent or a precursor of it is incorporated into the primary alcohol before sulphation, it is preferred to incorporate a compound of the formula:

where $R^1$, n and A are as defined previously. This compound is then sulphated at the same time as the primary alcohol, so that the sulphated mixture contains as stabilising agent a compound of the formula:

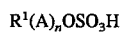

In corporation into the primary alcohol before sulphation thereof may be brought about by treating that alcohol with alkylene oxide, so as to convert the feedstock which contains a alcohol into a mixture of alcohol and alkoxylated alcohol. This mixture corresponds to a general formula:

$$R(A)_p OH$$

where p has an average value which preferably lies in the range 0.1 to 0.5.

If alcohol ethoxylate of formula $R^1(A)_n OH$ is made separately and added before sulphation, or if an alkyl ether sulphuric acid of formula $R^1(A)_n OSO_3H$ is added after or before sulphation, it is desirable that the eventual mixture of alkyl sulphuric acid and alkyl ether sulphuric acid corresponds to a general formula:

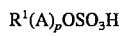

where p again has an average value of 0.1 to 0.5.

When the stabilising agent or a precursor thereof is included in the feedstock before Sulphation, either by addition to the primary alcohol or by exposure of the primary alcohol to an alkylene oxide, the amount of alkoxylated compound included in the eventual feedstock is restricted by the requirement that the proportion of alcohol in the feedstock shall exceed the proportion of compounds which include alkylene oxide or hydroxyalkyleneoxy groups.

It may be noted that the conventional manufacture of alkyl ether sulphate entails the sulphation of an alkoxylated alcohol which includes a proportion (which may be fairly small) of the alcohol itself. In such manufacture, the resulting alcohol sulphuric acid has been only a minor component of little importance.

If the feedstock contains only a small proportion (or none at all) of material other than the alcohol and any compounds which contain alkylene oxide or hydroxyalkyleneoxy groups, then the product of reaction will contain a majority by weight of primary alkyl sulphuric acid. This is a significant form of the invention.

Although the present invention requires that the feedstock contains the alcohol in larger amount than compounds (if any) which contain alkylene oxide residues or hydroxyalkyleneoxy group, it is possible that other materials may be present in the feedstock. Moreover these may undergo reaction.

Notably the feedstock may contain another material which undergoes sulphation or sulphonation, simultaneously with the sulphation of the primary alcohol. In particular the feedstock could contain alkylbenzene which undergoes sulphonation to alkylbenzene sulphuric acid. The product of reaction would then be a mixture of the acid forms of primary alkyl sulphate and alkylbenzene sulphonate.

The eventual mixture of PAS acid and stabilising agent produced by this invention may be stored for several hours, at least, before neutralisation. The lifetime of the PAS acid before significant decomposition has taken place is significantly extended by incorporation of stabilising agent in accordance with this invention when storage is at any of a range of temperatures, e.g. 0° C. to 40° C. If, however, storage is at a temperature towards the lower end of this range, preferably 0° C. to 20° C. more preferably 0° C. to 10° C., especially 0° C. to 5° C. the rate of the decomposition reaction will be reduced by the lower temperature as well as through the stabilising action. Consequently, the duration of storage in the presence of stabilising agent may be increased relatively to the possible duration of storage at a higher temperature with the same stabilising agent present. The use of low temperatures is also very valuable for inhibiting the formation of dioxan which, as mentioned earlier is an undesirable contaminant.

Incorporation of the stabilising agent in the PAS acid at a temperature at which the PAS acid is liquid is preferred.

In the following examples all quantities and percentages are by weight unless otherwise stated.

EXAMPLE 1

This example commenced with a fatty alcohol of formula:

ROH in which R was a mixture of straight and branched alkyl groups (about 60% branched), mainly of 12 and 13 carbon atoms. This alcohol, made by the OXO process, was commercially available as LIAL 123.

The alcohol was sulphated using sulphur trioxide and a pilot plant falling film reactor. Three batches of the resulting PAS acid were collected from the following film reactor. One batch was maintained at 30° C. for 24 hours. A second batch was maintained at 10° C. for the same period. A third batch was immediately mixed with nonionic surfactant as stabilising agent in an amount which formed 15% of the resulting mixture (i.e. an 85:15 weight ratio of reaction product:stabilising agent). It was then also stored at 10° C. This nonionic surfactant was coconut alcohol (mainly $C_{12}$ and $C_{14}$) ethoxylated under reaction conditions which yield a high proportion of molecules with up to four ethylene oxide residues and a very small proportion with six or more ethylene oxide residues. This was a so-called "peaked nonionic" in accordance with the general formula:

$$R^1(A)_nOH$$

with $R^1$ mostly $C_{12}$ and $C_{14}$ linear alkyl,

A denoting an ethylene oxide residue, and n having an average value of 2.0.

Portions were taken from each batch of PAS acid at intervals, neutralised with sodium hydroxide solution and analysed for content of sulphate detergent (SD) and for sulphate-free organic matter (SFOM).

The neutralisation conditions were calculated such as to give an aqueous liquor with a theoretical anionic detergent content of approximately 25% by weight.

The analytical results for sulphate-free organic matter are quoted as a percentage of the quantity of anionic detergent found by analysis.

Portions from the third batch were also analysed for dioxan content. The amounts of this contaminant were expressed as parts per million based on the quantity of anionic detergent found by analysis.

The following results were obtained:

| Storage Time | 30° C. SD (%) | 30° C. SFOM (%) | 10° C. SD (%) | 10° C. SFOM (%) | 10° C. + coconut 2EO SD (%) | 10° C. + coconut 2EO SFOM (%) | 10° C. + coconut 2EO Dioxan (ppm) |
|---|---|---|---|---|---|---|---|
| Zero | 23.1 | 3.9 | 23.1 | 3.5 | 22.1 | 15.2 | <10 |
| 15 Mins | 20.5 | 4.4 | | | | | |
| 30 Mins | 19.9 | 5.0 | | | 20.5 | 15.1 | <10 |
| 45 Mins | 20.1 | 5.5 | | | | | |
| 1 Hour | 19.8 | 7.1 | 22.0 | 3.6 | 20.2 | 14.2 | 10 |
| 2 Hours | 19.1 | 6.3 | 21.7 | 3.7 | 20.2 | 14.1 | 23 |
| 4 Hours | 16.7 | 13.8 | | | 20.4 | 14.4 | 18 |
| 6 Hours | | | | | 20.2 | 14.3 | 27 |
| 24 Hours | 16.3 | 18.7 | 20.5 | 5.9 | 20.1 | 14.5 | 41 |

It can be seen from these results, especially the rinsing values for sulphate-free organic matter, that without the stabilising agent spontaneous decomposition is considerable at 30° C. and still significant at 10° C.

With stabilising agent added the decomposition is less. The figure for anionic sulphate detergent (SD) starts lower because of the addition of stabilising agent. It then decreases to a smaller extent than is the case without stabilising agent. The figure for sulphate-free organic matter is higher because stabilising agent appears in this. The figure drops initially, which is attributed to small quantities of unreacted alcohol and sulphur trioxide in the PAS acid reaction product. When the reaction product is stirred before neutralisation some of the sulphur trioxide is able to react with the stabilising agent and this causes the small drop in the value for SFOM. Thereafter the value for SFOM remains almost constant.

An "ideal" value for SFOM was calculated on the basis of two assumptions:

1) the sulphation would yield a mixture containing small amounts of unreacted sulphur trioxide and alcohol (as normally observed) so that if neutralised prior to any decomposition of the PAS acid it would lead to a PAS:alcohol:$Na_2SO_4$ ratio of 100:1.5:1.5;

2) the unreacted sulphur trioxide would combine with some of the stabilising agent, thus converting it to detergent.

The value of SFOM predicted in this way was 14.6%, close to the observed values.

EXAMPLE 2

This example used a commercial fatty alcohol (LIAL 125) of formula:

ROH where R was a mixture of straight and branched alkyl groups, mainly of 12 to 15 carbon atoms.

It was sulphated as in Example 1. Three batches were collected and held at 0° to 5° C.

No stabilising agent was added to one batch. A second of these batches was immediately mixed with a stabilising agent which was the same as used in Example 1. This was pre-cooled to a temperature below 5° C. before addition. It was added in an amount providing 15% by weight of the resulting mixture, as in Example 1.

The third batch was likewise immediately mixed with a stabilising agent in an amount providing 15% by weight of the resulting mixture. This stabilising agent was again a peaked nonionic surfactant obtained by ethoxylation of LIAL 125. It was in accordance with a general formula:

$R(A)_n OH$ where R is the same as for LIAL 125, A denotes an ethylene oxide residue and n has an average value of 2.0.

Portions were taken from each batch at intervals and neutralised with sodium hydroxide at under conditions calculated to give an aqueous liquor with a theoretical anionic detergent content of approximately 20% by weight.

The resulting neutralised samples were analysed and results are given below for Content of sulphate detergent (SD). For the batches which received stabilising agent results are also given for sulphate-free organic matter (SFOM) and dioxan content. As in the previous example, these results are given as percentages and parts per million of the quantity of anionic detergent found by analysis.

It was then sulphated as in Example 1. Four batches were collected. One was held at 20° C. another was held at 0° C. to 3° C. Two others were mixed with a further stabilising agent in an amount which was 15% of the overall mixture. This further stabilising agent was LIAL 125, ethoxylated to contain an average of two ethylene oxide residues as used in Example 2 and held at 20° C. and at 0° C. to 3° C. respectively.

Portions from each batch were removed, neutralised and analysed as in the previous example. Results obtained are set out in the following Table:

The "ideal" value for SFOM, calculated as in Example 1, when stabiliser was present, was 14.5%.

| Storage Time | No Stabiliser | | + coconut 2EO | | | + $C_{12}$–$C_{15}$ alcohol 2EO | | |
|---|---|---|---|---|---|---|---|---|
| | SD (%) | SFOM (%) | SD (%) | SFOM (%) | Dioxan | SD (%) | SFOM (%) | Diosan |
| Zero | 21.1 | 1.5 | 19.8 | 17.5 | ND | 18.8 | 16.2 | ND |
| 4 hours | — | — | — | — | — | 15.8 | 17.2 | ND |
| 4.5 hours | — | — | 19.8 | 14.8 | ND | — | — | — |
| 5 hours | 17.7 | 4.6 | — | — | — | — | — | — |
| 18 hours | — | — | — | — | — | 16.6 | 17.2 | ND |
| 22 hours | — | — | 18.7 | 16.6 | ND | — | — | — |

(ND means dioxan was below a detection limit of 15 ppm based on the quantity of anionic detergent).

As can be seen from these results, with stabilising agent added at low temperature the decomposition is reduced and dioxan formation is low.

EXAMPLE 3

This example also used a LIAL 125 fatty alcohol. It was ethoxylated to comply with a general formula:

$R(OCH_2CH_2)_p OH$ where p had an average value of 0.25.

| Storage | 20° C. no Stabiliser added after sulphation | | | 0° C. no stabiliser added after sulphation | | | 20° C. with stabiliser added after sulphation | | | 0° C. with stabiliser added after sulphation | | |
|---|---|---|---|---|---|---|---|---|---|---|---|---|
| Time | SD | SFOM | Dioxan | SD | SFOM | Diosan | SD | SFOM | Dioxan | SD | SFOM | Dioxan |
| Zero | 24.8 | 2.6 | <10 | 25.1 | 3.6 | <10 | 217 | 17.5 | 40 | 21.8 | 17.4 | 9 |
| 30 Min | 24.7 | 6.0 | 57 | — | — | — | 22.1 | 15.0 | 64 | — | — | — |
| 1 Hour | 23.9 | 8.4 | 177 | 25.1 | 4.4 | 45 | 21.7 | 14.3 | 61 | 21.9 | 13.2 | 22 |
| 2 Hrs | 22.1 | 8.2 | 196 | 24.7 | 5.3 | 54 | 22.2 | 14.4 | 60 | 22.5 | 16.0 | 32 |
| 4 Hrs | 22.5 | 9.8 | 196 | 24.5 | 5.3 | 89 | 21.5 | 15.4 | 73 | 22.3 | 13.9 | 25 |
| 6 Hrs | 21.6 | 11.3 | 175 | 24.3 | 6.2 | 123 | 22.3 | 14.8 | 72 | 21.8 | 13.7 | 25 |
| 24 Hrs | 18.0 | 22.7 | 491 | 24.5 | 4.8 | 141 | 21.2 | 15.1 | 235 | 21.9 | 14.6 | 74 |
| 3 Days | 16.1 | 29.2 | 1031 | 23.0 | 9.1 | 226 | 20.5 | 20.0 | 705 | 22.6 | 14.4 | 66 |

The results in the first two columns are for a system where the stabiliser was the alkyl sulphuric acid product of the ethoxylated alcohol present in the starting alcohol. These results show an improvement compared with the results without any stabiliser in the previous examples, showing the benefit of including the alkyl ether sulphuric acid. However, the addition of nonionic surfactant as stabiliser after sulphonation gave a considerable further improvement.

EXAMPLE 4

LIAL 123 was sulphated to produce PAS acid as in Example 1. Stabilising agent was then added to a batch of PAS acid no provide a weight ratio of 85:15 of reaction product to stabilising agent and maintained at a constant temperature as listed below.

| Stabilising Agent | Temperature | | |
|---|---|---|---|
| | 8° C. | 20° C. | 30° C. |
| A | 4.1 | 4.2 | — |
| B | 4.3 | 4.4 | 4.5 |
| C | 4.6 | — | — |
| D | 4.7 | — | — |

A: LIAL 123 having an average degree of ethoxylation of 3
B: LIAL 125 having an average degree of ethoxylation of 2
C: LIAL 125 having an average degree of ethoxylation of 3
D: Coconut oil having an average degree of ethoxylation of 3
B, C and D were narrow range ethoxylates.

Samples were then taken periodically from each batch and neutralised as in Example 2 and analysed to determine the amount of non-detergent organic matter (NDOM) and the level of dioxan therein. The results are listed in the following tables and the NDOM figures are % by weight and ppm based on the quantity of anionic detergent detected.

| Time | Batch 4.1 | | Batch 4.2 | |
|---|---|---|---|---|
| (Hours) | NDOM | Dioxan | NDOM | Dioxan |
| 2 | 6 | 47 | 8.3 | 103 |
| 4 | 6.9 | 8 | | 132 |
| 6 | 6.1 | | 7.7 | 161 |
| 24 | 6.8 | 47 | 8.8 | 216 |

-continued

| | Batch | | | | | |
|---|---|---|---|---|---|---|
| Time | 4.3 | | 4.4 | | 4.5 Di- | 4.6 Di- | 4.7 Di- |
| (Hrs) | NDOM | Dioxan | NDOM | Dioxan | oxan | oxan | oxan |
| 24 | 10.4 | 5 | 11.9 | 122 | 356 | 37 | 38 |
| 48 | 10.6 | 87 | 12.9 | 308 | 478 | 54 | 81 |
| 96 | 11.5 | 170 | | | | | |
| 120 | 11.5 | 165 | | | | | |

The above NDOM figures do not vary significantly with time thus indicating that the PAS acid does not decompose to any significant extent. Further the results show that dioxane formation is suppressed by storing the batch at lower temperature and by employing a narrow range ethoxylate as a stabilising agent.

EXAMPLE 3

LIAL 125 alcohol was sulphated to produce PAS acid of at least 97% purity, 2 batches of PAS acid were collected and mixed together with a stabilising agent in a weight ratio of 85:15 and maintained at a temperature of 0° to 5° C. The stabilising agents employed were LIAL 125 having an average degree of ethoxylation of 2 (narrow range (Batch 5.1) and a methyl end-capped nonionic surfactant having an average degree of ethoxylation of 6.5 and available under the trade name REWOPAL MT65 from REWO (Batch 5.2).

Samples were taken from each batch after 1 hour and 24 hours and neutralised as in Example 2 and analysed to determine NDOM and dioxan levels.

The results are shown below.

| Time | 5.1 | | 5.2 | |
|---|---|---|---|---|
| (hours) | NDOM | Dioxan | NDOM | Dioxan |
| 1 | 8.65 | 24 | 8.8 | 35 |
| 24 | 8.2 | 4 6 | 9.3 | 54 |

The results show that the PAS acid does not decompose significantly and dioxan levels are kept at a low level with time. Additionally the stabilising agent in Batch 5.2 has a higher degree of ethoxylation than that in Batch 5.1. This would be expected to give a higher level of dioxans. However, the results show only a marginal difference in dioxan formation thus illustrating the beneficial effect of employing an end-capped stabilising agent.

We claim:

1. A method of preparing primary alkyl sulphuric acid having the formula:

$$ROSO_3H$$

where R is a straight or branched saturated primary alkyl group of 8 to 22 carbon atoms which method comprises sulphating a feedstock comprising the corresponding primary alcohol of formula:

$$ROH$$

to produce a sulphated reaction product, and incorporating in the reaction product as a stabilising agent a compound or mixture of compounds of the formula:

$$R^1(A)_nOX$$

where

R$^1$ is a straight or branched primary alkyl group of 8 to 22 carbon atoms,

A is a lower alkylene oxide residue containing 2 to 4 carbon atoms, n is in the range 0.5 to 4, and X is hydrogen, —OSO$_3$H or an alkyl group of 1 to 8 carbon atoms the proportion by weight of the alcohol ROH in the feedstock exceeding the proportion by weight, if any, of compounds which include alkylene oxide residues or hydroxyalkyleneoxy groups in the feedstock.

2. A method according to claim 1 wherein the weight ratio of the primary alkyl sulphuric acid and the stabilising agent lies in a range from 20:1 to 2:1.

3. A method according to claim 1 wherein the said group R is a straight or branched saturated primary alkyl group of 8 to 15 carbon atoms.

4. A method according to claim 1 wherein the stabilising agent incorporates alkylene oxide residues of formula:

$$—OCH_2(CH_2)_m—$$

where m is an integer from 1 to 3.

5. A method according to claim 1 wherein stabilising agent is added to the reaction product after sulphation.

6. A method according to claim 1 wherein one or a mixture of compound(s) which include alkylene oxide residues or glycidyl groups is incorporated in the primary alcohol so as to provide stabilising agent in the reaction product after sulphation.

7. A method according to claim 6 wherein the primary alcohol is treated with alkylene oxide before sulphation so as to correct it to a mixture of compounds of formula:

$$R(A)_pOH$$

where A denotes an alkylene oxide residue of formula —OCH$_2$(CH$_2$)$_m$— in which m is from 1 to 3, and p has an average value of not more than 0.5.

8. A method according to claim 5 wherein X is hydrogen or a lower alkyl group of 1 to 4 carbon atoms.

* * * * *